(12) United States Patent
Greenhalgh et al.

(10) Patent No.: US 10,292,747 B2
(45) Date of Patent: May 21, 2019

(54) BONE GRAFT DELIVERY SYSTEM AND METHOD FOR USING SAME

(71) Applicant: SurGenTec, LLC, Boca Raton, FL (US)

(72) Inventors: Travis Greenhalgh, Boca Raton, FL (US); Ryan Lewis, Waxhaw, NC (US)

(73) Assignee: SurGenTec, LLC, Boca Raton, FL (US)

( * ) Notice: Subject to any disclaimer, the term of this patent is extended or adjusted under 35 U.S.C. 154(b) by 0 days.

(21) Appl. No.: 15/495,794

(22) Filed: Apr. 24, 2017

(65) Prior Publication Data
US 2017/0354514 A1    Dec. 14, 2017

Related U.S. Application Data

(63) Continuation of application No. 14/611,718, filed on Feb. 2, 2015, now Pat. No. 9,655,748, which is a continuation of application No. 14/162,102, filed on Jan. 23, 2014, now Pat. No. 8,945,137.

(60) Provisional application No. 61/798,513, filed on Mar. 15, 2013.

(51) Int. Cl.
| | |
|---|---|
| *A61B 17/88* | (2006.01) |
| *A61F 2/46* | (2006.01) |
| *A61B 17/00* | (2006.01) |
| *A61B 17/16* | (2006.01) |

(52) U.S. Cl.
CPC .... *A61B 17/8802* (2013.01); *A61B 17/00234* (2013.01); *A61B 17/1635* (2013.01); *A61B 17/8811* (2013.01); *A61F 2/4601* (2013.01); *A61B 17/1631* (2013.01); *A61B 17/1659* (2013.01); *A61B 2017/00407* (2013.01)

(58) Field of Classification Search
CPC  A61B 17/8802; A61B 17/8811; A61F 2/4455
See application file for complete search history.

(56) References Cited

U.S. PATENT DOCUMENTS

| | | | |
|---|---|---|---|
| 2,316,095 A | * | 4/1943 | Mead, Jr. ............... A61M 5/24 604/209 |
| 4,277,184 A | * | 7/1981 | Solomon ............ A61B 17/8822 366/139 |
| 4,338,925 A | | 7/1982 | Miller |
| 5,531,749 A | | 7/1996 | Michelson |

(Continued)

OTHER PUBLICATIONS

Third Party Submission Under 37 CFR 1.290 dated Apr. 4, 2017 in U.S. Appl. No. 14/992,954.

(Continued)

*Primary Examiner* — Andrew Yang
(74) *Attorney, Agent, or Firm* — Knobbe Martens Olson & Bear, LLP

(57) ABSTRACT

A bone graft delivery system can include an elongate tube, a handle having a trigger, and a tip. The trigger is actuated to deliver bone graft material through the tube. The tip has one or more openings to deliver the bone graft material to a desired location and includes a surface suitable to act as a rasp for decorticating bone. A method for delivering bone graft material to a desired surgical location includes providing a bone graft delivery device, positioning the device adjacent the surgical location, decorticating bone, and delivering bone graft material to the surgical location.

20 Claims, 17 Drawing Sheets

(56) References Cited

U.S. PATENT DOCUMENTS

| | | |
|---|---|---|
| 5,733,288 A | 3/1998 | Allen |
| 6,439,439 B1 | 8/2002 | Rickard et al. |
| 6,814,736 B2 | 11/2004 | Reiley et al. |
| 7,141,054 B2 | 11/2006 | Vandewalle |
| 7,306,603 B2 | 12/2007 | Boehm, Jr. et al. |
| 7,513,901 B2 | 4/2009 | Scifert et al. |
| 7,799,033 B2 | 9/2010 | Assell et al. |
| 7,811,291 B2 | 10/2010 | Liu et al. |
| 7,887,543 B2 | 2/2011 | Sand et al. |
| 8,308,805 B2 | 11/2012 | Lynn et al. |
| 8,628,536 B2 | 1/2014 | Walker et al. |
| 8,932,295 B1 | 1/2015 | Greenhalgh |
| 8,945,137 B1 | 2/2015 | Greenhalgh et al. |
| 9,173,694 B2 * | 11/2015 | Kleiner .............. A61B 17/8819 |
| 9,668,881 B1 | 6/2017 | Greenhalgh et al. |
| 2004/0024409 A1 | 2/2004 | Sand et al. |
| 2004/0133211 A1 | 7/2004 | Raskin et al. |
| 2004/0215201 A1 | 10/2004 | Lieberman |
| 2005/0107800 A1 | 5/2005 | Frankel et al. |
| 2005/0137604 A1 | 6/2005 | Assell et al. |
| 2005/0171549 A1 | 8/2005 | Boehm, Jr. et al. |
| 2005/0203523 A1 | 9/2005 | Wenstrom, Jr. et al. |
| 2006/0293687 A1 | 12/2006 | Bogert |
| 2007/0005072 A1 | 1/2007 | Castillo et al. |
| 2007/0276397 A1 | 11/2007 | Pacheco |
| 2007/0289998 A1 | 12/2007 | Keller |
| 2008/0065082 A1 | 3/2008 | Chang et al. |
| 2008/0071284 A1 | 3/2008 | Lechmann |
| 2008/0125856 A1 | 5/2008 | Perez-Cruet et al. |
| 2008/0300684 A1 | 12/2008 | Shelokov |
| 2009/0216238 A1 | 8/2009 | Stark |
| 2009/0318925 A1 | 12/2009 | Campion et al. |
| 2010/0036381 A1 | 2/2010 | Vanleeuwen |
| 2010/0057087 A1 | 3/2010 | Cha |
| 2010/0174286 A1 | 7/2010 | Truckai et al. |
| 2010/0179556 A1 | 7/2010 | Scribner |
| 2010/0204702 A1 | 8/2010 | Lechot et al. |
| 2010/0262146 A1 | 10/2010 | Tulkis |
| 2011/0071527 A1 | 3/2011 | Nelson et al. |
| 2011/0071536 A1 | 3/2011 | Kleiner et al. |
| 2012/0253316 A1 | 10/2012 | Oktavec et al. |
| 2014/0252044 A1 | 9/2014 | Greter et al. |
| 2015/0105748 A1 | 4/2015 | McBride et al. |
| 2015/0190148 A1 | 7/2015 | Greenhalgh |
| 2015/0209156 A1 | 7/2015 | Greenhalgh et al. |

OTHER PUBLICATIONS

Globus Medical Allocate product, http://www.globusmedical.com/portfolio/allocate/, 2014, 2 pp.

* cited by examiner

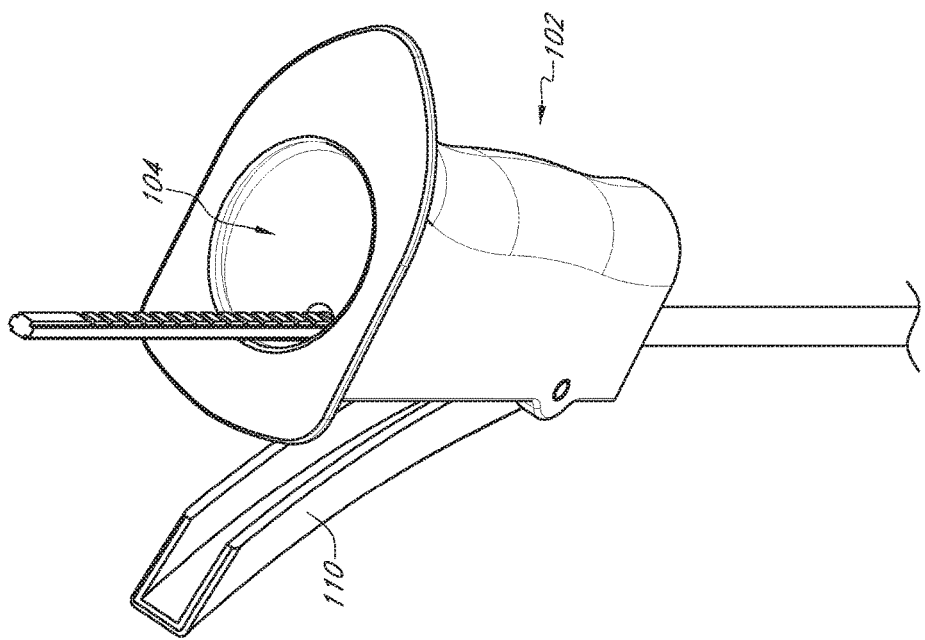

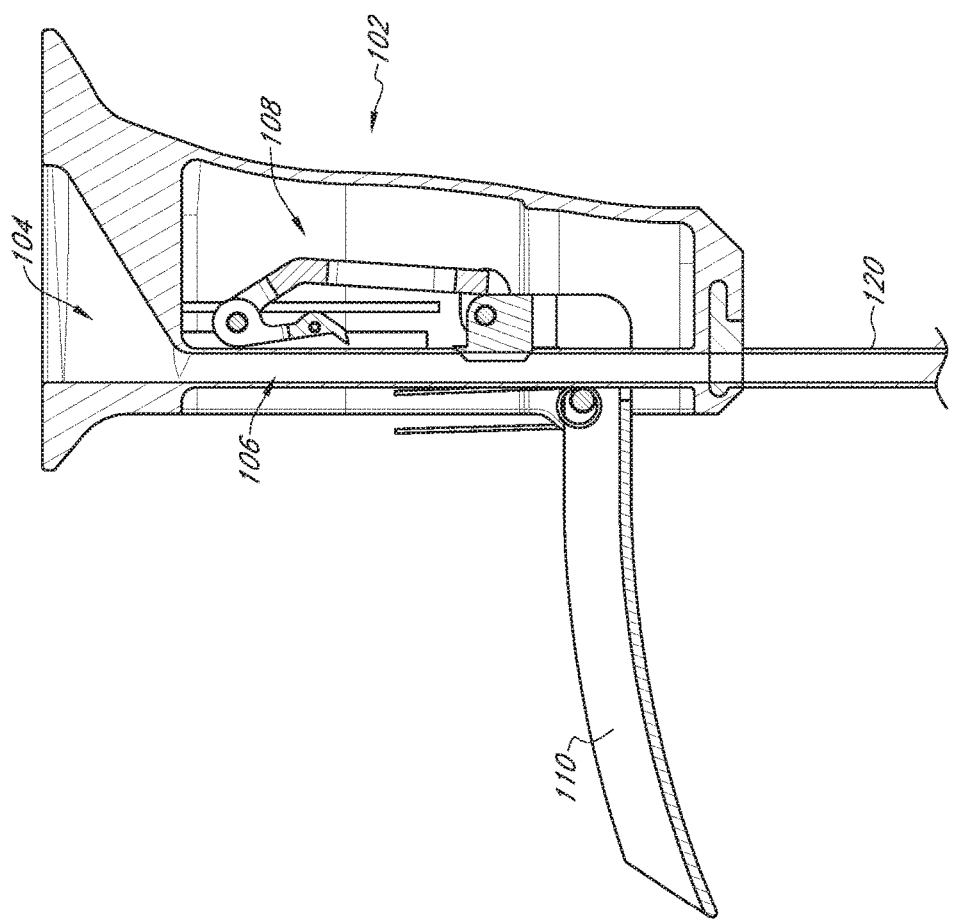

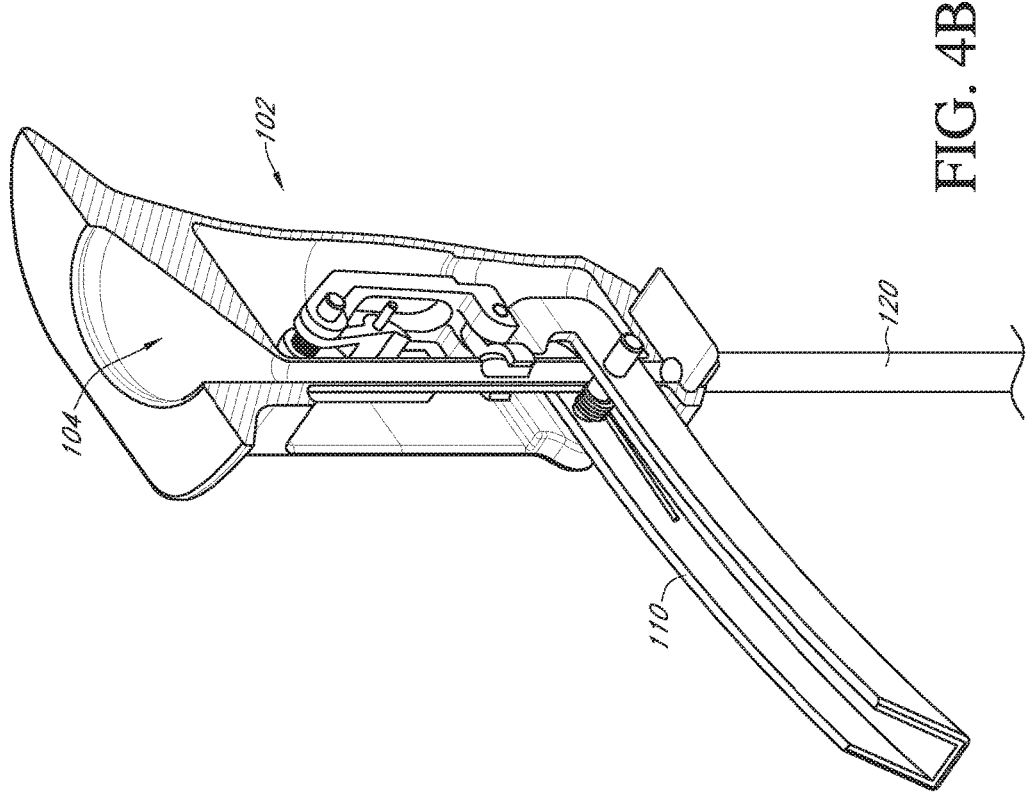

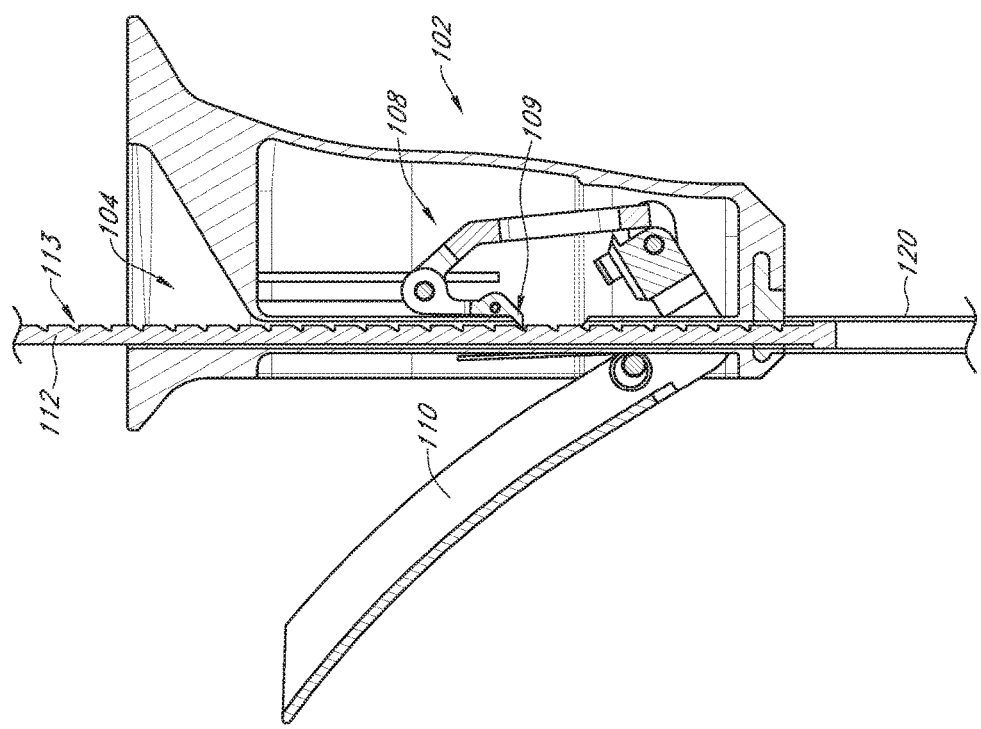

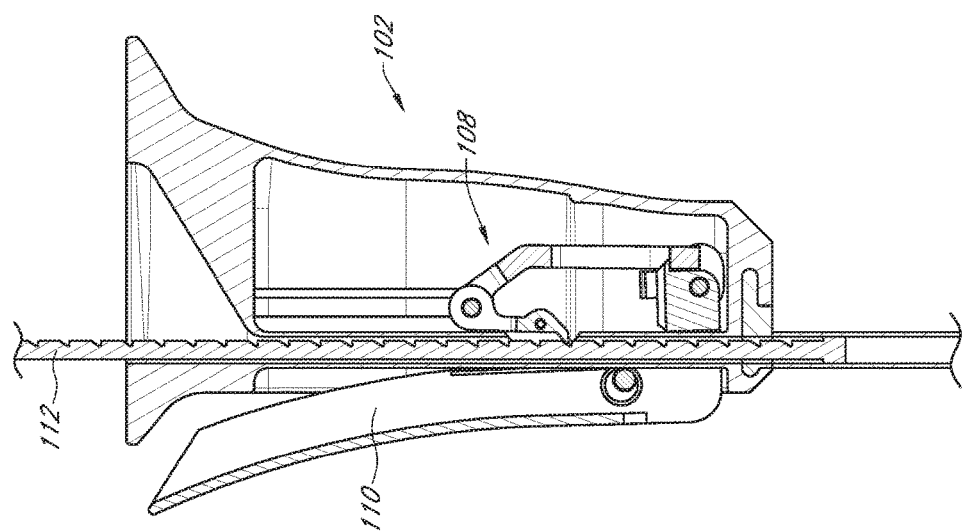

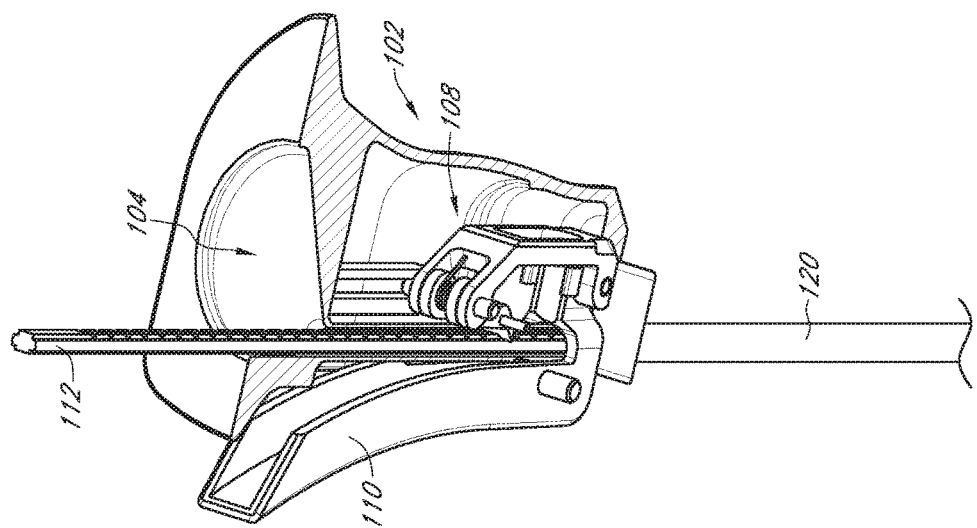

BONE GRAFT DELIVERY SYSTEM AND METHOD FOR USING SAME

CROSS-REFERENCE TO RELATED APPLICATIONS

This application is a continuation of U.S. application Ser. No. 14/611,718, filed Feb. 2, 2015, which is a continuation of U.S. application Ser. No. 14/162,102, filed Jan. 23, 2014, which claims priority benefit of U.S. Provisional Application No. 61/798,513, filed Mar. 15, 2013, the entirety of each of which is hereby incorporated by reference herein and should be considered a part of this specification.

BACKGROUND

Field

The present application relates to orthopedic surgery in general, and more particularly, to bone graft delivery systems and methods.

Description of the Related Art

In a bone grafting procedure, a surgeon places bone or a bone substitute into an area in a patient's body to provide a type of scaffold for bone growth and repair. Bone grafts can be used to help treat various orthopedic problems, for example, to fuse a joint or repair a fracture. Bone graft material can be, for example, autogenous (harvested from the patient's own body), allogeneic (harvested from another person, usually a cadaver), or synthetic. Many bone grafting procedures are performed via open surgery implantation. However, these procedures can be performed minimally invasively, for example, by using a needle to inject the bone graft material into the target location without requiring a surgical incision.

In some cases decortication of the bony area receiving the graft is performed prior to delivery of the bone graft material. Decortication removes superficial cortical bone and exposes the underlying cancellous bone, which can help accelerate the integration of the bone graft with the native bone.

SUMMARY

The devices, systems, and methods described herein allow for minimally invasive delivery of bone graft material to a desired location in a patient's body. In some embodiments, the devices, systems, and methods described herein also provide for bone decortication.

In some embodiments, a bone graft delivery system includes an elongate tube, a handle at a proximal end of the tube configured to be actuated to deliver bone graft material through the tube, and a tip at a distal end of the tube. The handle may include a trigger. The tip includes one or more openings configured to deliver the bone graft material to a desired location and a surface suitable to serve as a rasp for scraping bone.

In some embodiments, a method for delivering bone graft material to a surgical location includes providing a bone graft delivery device comprising an elongate tube and a distal tip having at least one opening for delivering the bone graft material to the surgical location and positioning the device adjacent the surgical location. The method further includes decorticating bone with the distal tip and delivering bone graft material through the tube and out the at least one opening of the tip.

BRIEF DESCRIPTION OF THE DRAWINGS

FIG. 3 illustrates a perspective view of a handle of the bone graft delivery device of FIG. 1;

FIGS. 4A-4E are section views illustrating operation of a ratcheting mechanism in the handle of FIG. 3;

DETAILED DESCRIPTION

Figure 1:
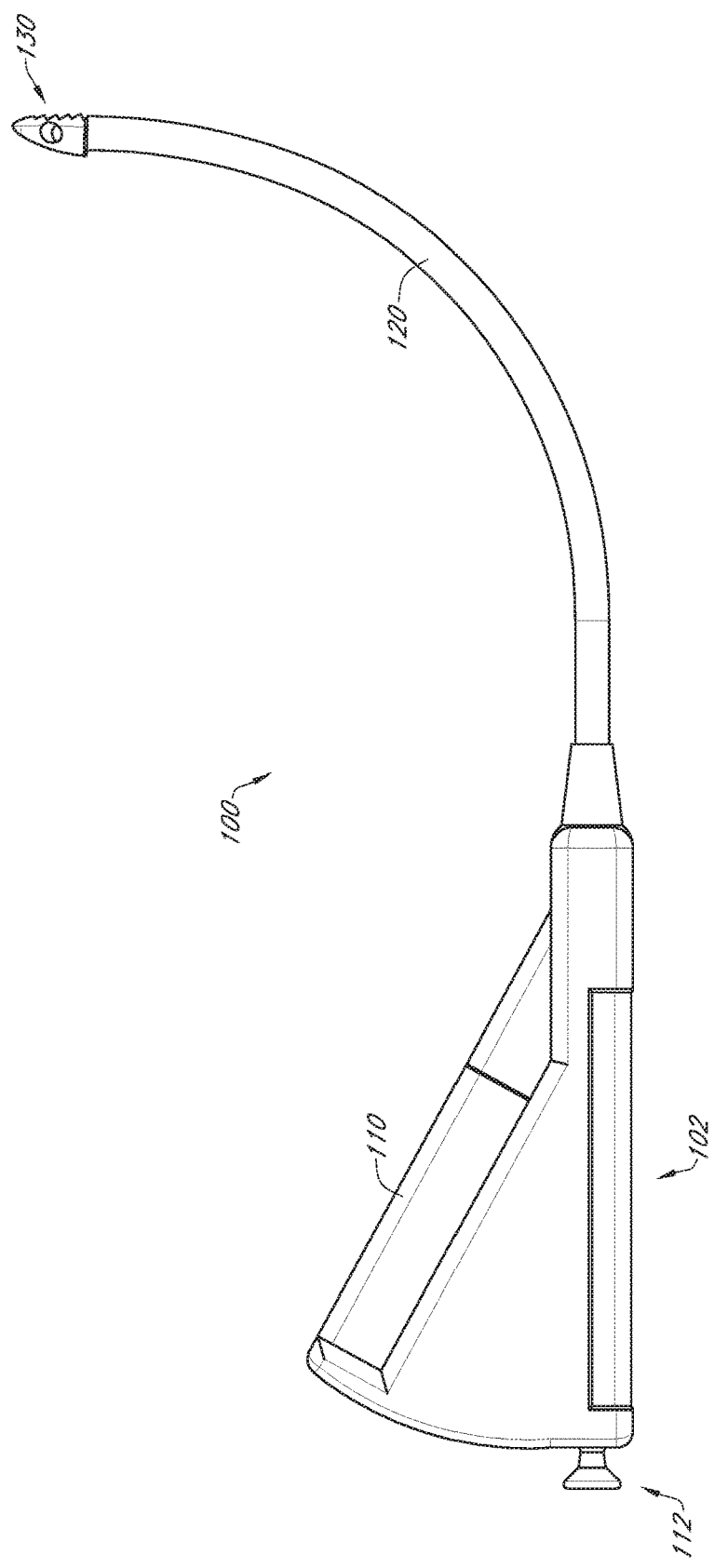
FIG. 1 illustrates a side view of an example embodiment of a bone graft delivery device.
Figure 2:
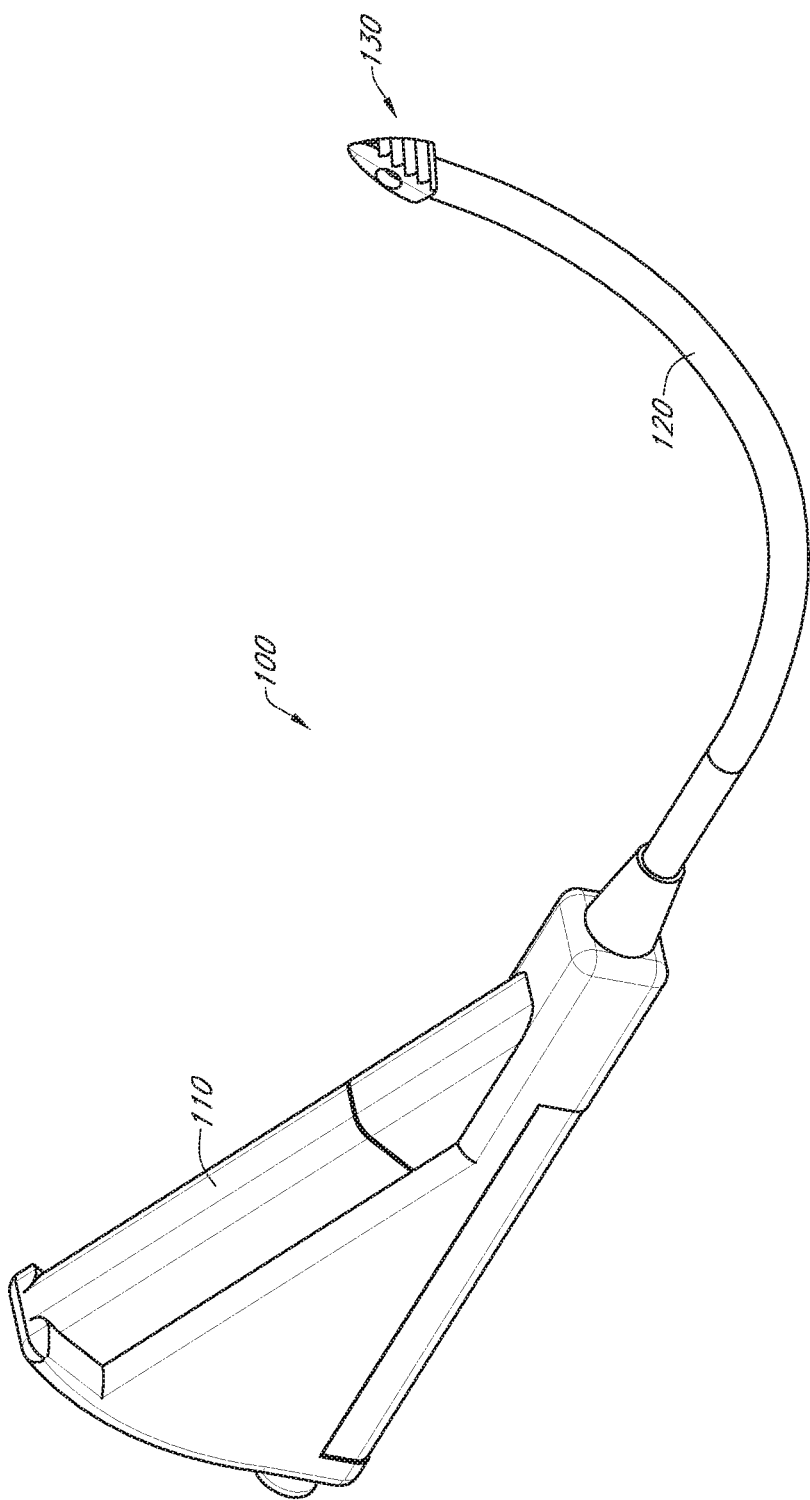
FIG. 2 illustrates a perspective view of the bone graft delivery device of FIG. 1.

As shown in FIGS. 1 and 2, a bone graft delivery device 100 generally includes a handle 102 having a trigger 110 or other actuation mechanism, a tube 120 having a lumen therethrough, and a distal tip 130. In the illustrated embodiment, the bone graft delivery device 100 is similar to a caulking gun. The handle 102 can house a supply of the desired bone graft material. The bone graft material can be pre-loaded in the handle 102 or can be supplied to the handle via a cartridge that can be removably coupled to the handle 102. In some embodiments, the device 100 can further include a plunger 112 that is retracted proximally to allow the handle to receive a cartridge or pre-loaded volume of bone graft material.

In use, the trigger 110 is actuated to deliver bone graft material through the tube 120 and distal tip 130 to a desired surgical location. In some embodiments, the plunger 112 is simultaneously pushed distally to help deliver bone graft material through the tube 120. In some embodiments, the trigger 110 or other actuation mechanism is configured to deliver a controlled release amount of bone graft material during actuation of the device, for example, ½ cc of bone graft material per complete squeeze of the trigger 110. The trigger 110 or other actuation mechanism may be operated manually or by mechanical, battery powered, electric, pneumatic, or any other means of force.

In some embodiments, a base of the handle 102 can include a funnel 104 configured to receive the bone graft material, as shown in FIG. 3. Whereas some existing bone graft delivery devices are only compatible with certain, e.g., pre-packaged, bone graft materials, the funnel 104 can be designed to advantageously allow the user to use any bone graft material or combination of bone graft materials he or she wishes or deems appropriate. For example, the user can use synthetic, autologous, stem cell, DMB, cadaveric, and/or any other available bone graft material. The handle 102 can further include a channel 106 extending therethrough connecting and in fluid communication with the funnel 104 and tube 120. The user can mix the desired bone graft material in the funnel 104, then use the plunger 112 or other means to advance the bone graft material through the channel 106 and into the tube 120 for delivery.

In some embodiments, the handle 102 includes a ratcheting mechanism 108 configured to advance bone graft material from the funnel 104 and channel 106 through the tube 120 for delivery. As illustrated in FIGS. 4A and 4B, extending the trigger 110 away from the handle 102, for example to a position perpendicular to the handle 102, can place the ratcheting mechanism 108 in a closed position that does not allow interior access for the plunger 112 to allow for loading of the bone graft material through the funnel 104 into the channel 106. Once the bone graft material has been loaded, the trigger 110 can be moved toward the handle 102 to an intermediate position, as shown in FIG. 4C, to open the channel 106 and allow the plunger 112 to be inserted into the channel 106. An arm 109 of the ratcheting mechanism 108 engages one of a series of notches 113 on the plunger 112. Movement of the trigger 110 to a final position closest the handle 102 causes the arm 109 of the ratcheting mechanism 108 to move distally within the handle 102 (or away from the funnel 104 and toward the tube 120), thereby advancing the plunger 112 distally within the channel 106 to force the bone graft material distally within the channel 106 and/or tube 120, as shown in FIGS. 4D and 4E. The trigger 110 can be moved back to the intermediate position to cause the ratcheting mechanism 108 to move proximally within the handle 102 (or toward the funnel 104) and the arm 109 to slide proximally along the plunger 112 to engage a more proximal notch 112. The trigger 110 can be moved between the intermediate position and final position multiple times until the arm 109 has reached the proximal end of the plunger 112.

Figure 6A:
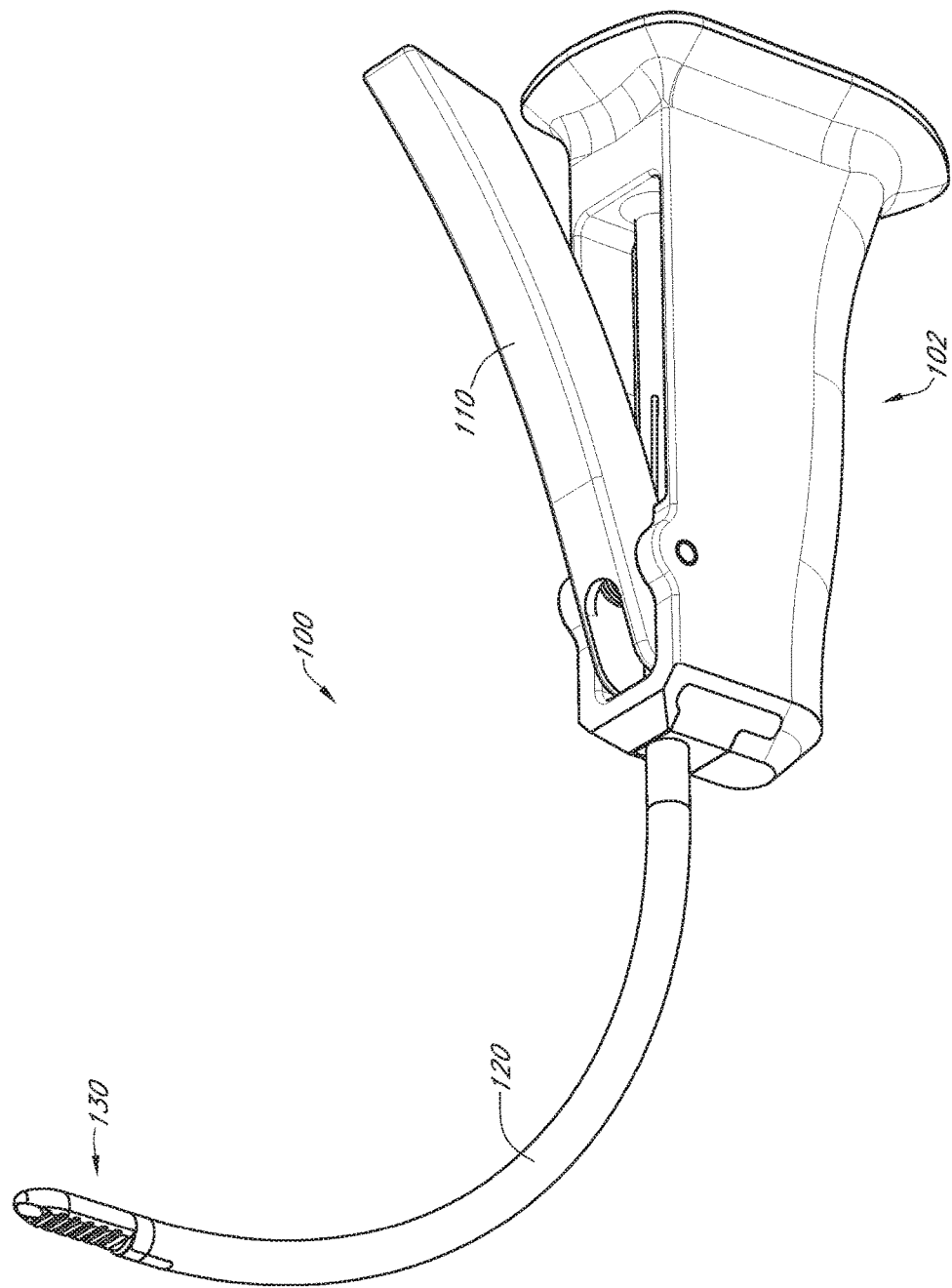
FIG. 6A illustrates a perspective view of an example embodiment of a bone graft delivery device.
Figure 6B:
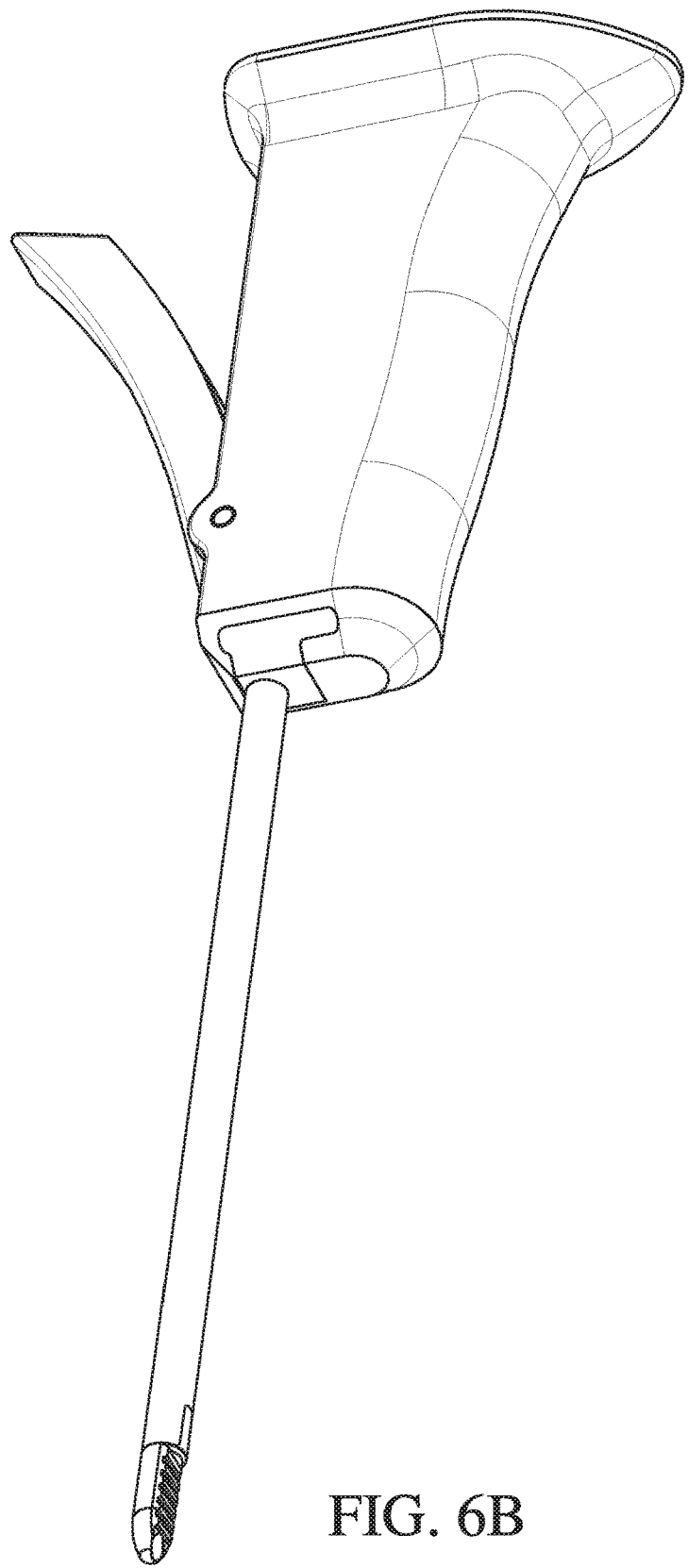
FIG. 6B illustrates a perspective view of an example embodiment of a bone graft delivery device.
Figure 6C:
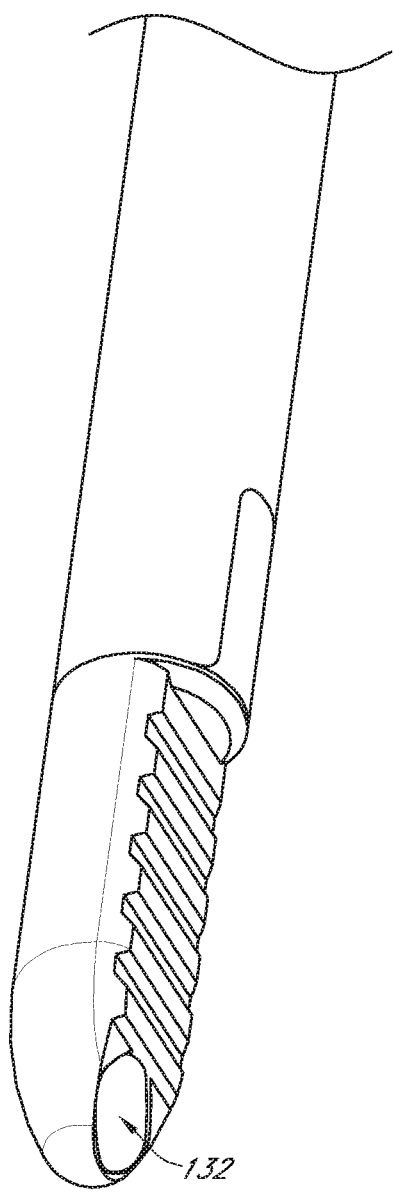
FIG. 6C illustrates an enlarged view of a distal tip of the bone graft delivery device of FIG. 6B.

As shown in FIGS. 1 and 2, the tube 120 can include a permanent bend or curve that may be useful in positioning the device 100 at a desired location, for example, a space between two spinal discs. Alternatively, the tube 120 may be straight, for example, as shown in FIG. 6B, to deliver bone graft material directly into a desired location such as a disc space. In some embodiments, the tube 120 is somewhat flexible or repositionable and can be manipulated to bend or curve the tube 120 as needed to reach the desired location. In some embodiments, the tube 120 is made of a rigid material, for example, a plastic, composite, or metal, and is generally hollow to allow for the passage of bone graft material through the tube 120.

Figure 5A:
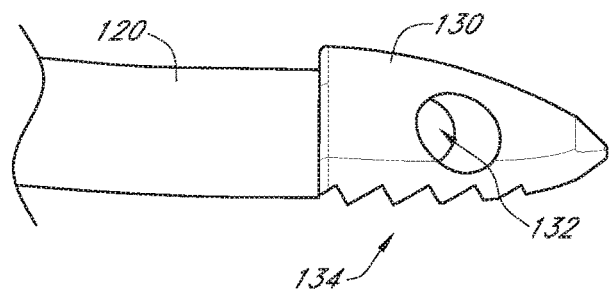
FIGS. 5A-5C illustrate various views of a distal tip of the bone graft delivery device of FIGS. 1 and 2.
Figure 5B:
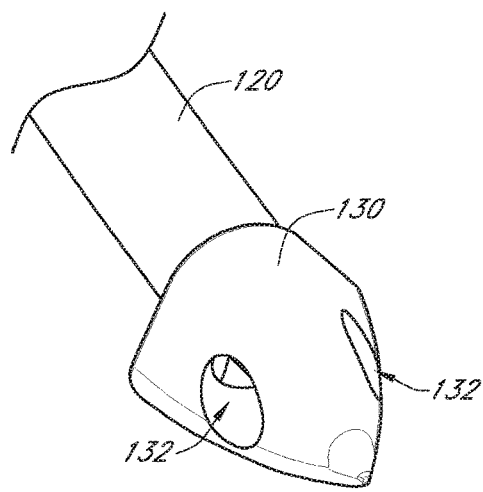
Figure 5C:
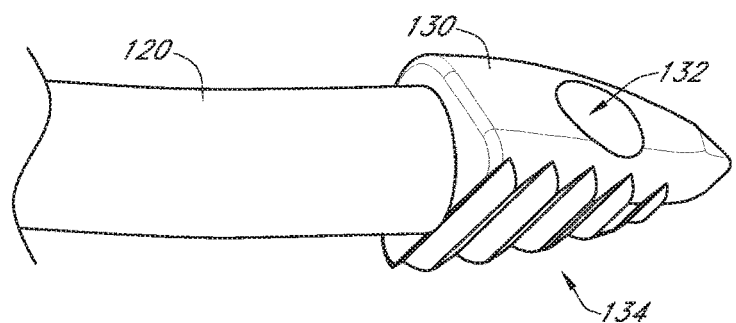
Figure 6D:
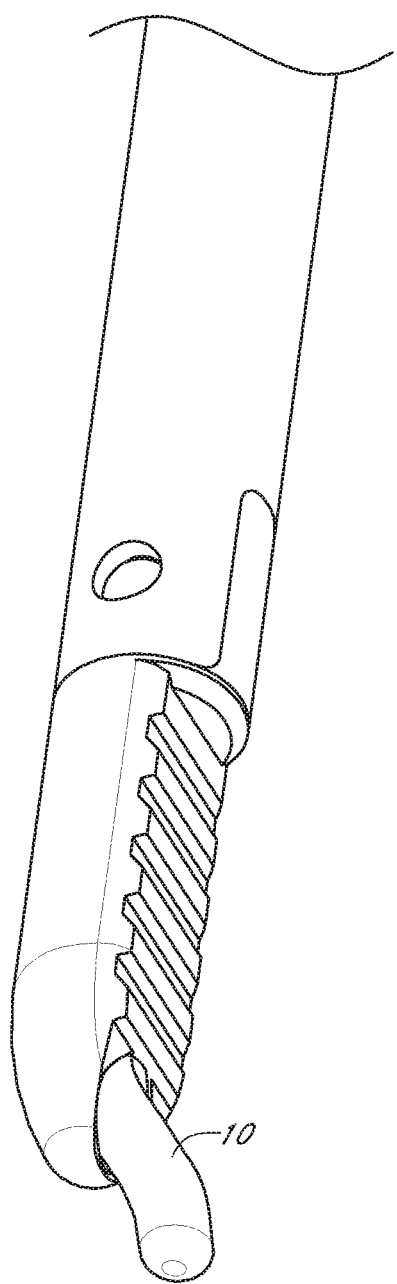
FIG. 6D illustrates the distal tip of FIG. 6C extruding bone graft material.

As shown in FIGS. 5A-5C, a distal end of the tube 120 includes a tip 130. The tip 130 can be integrally formed with or coupled, removably or permanently, to the tube 120. In the illustrated embodiment, the tip 130 is somewhat bullet-shaped with a generally triangular cross-section; however, other shapes and configurations are also possible. For example, the tip 130 can be generally flat as shown in the example embodiments of FIGS. 6A-6D. In some embodiments, the tip 130 is pointed and/or sharp to dissect or split muscle and tissue as it is advanced through the patient's skin and body to the surgical location. Alternatively, the tip 130 can be blunt to allow for displacement of muscle without risk of cutting of nerves or other tissue. The tip has a single or multiple openings 132 in fluid communication with the tube 120 lumen and configured to deliver the bone graft material 10 from the tube 120, as shown in FIG. 6D, to the desired location.

In some embodiments, at least one side or area of the tip 130 includes a series of jagged edges or other suitable surface 134 configured to serve as a rasp for scraping bone. The rasp may be operated manually or by mechanical, battery powered, electric, pneumatic, or any other means of force to allow for decortication of the area to receive the bone graft material.

In some embodiments, the delivery device 100 includes a sleeve slidably or telescopingly disposed over the tip 130. In some embodiments, the sleeve can extend to a proximal end of the tube 120 adjacent the handle 102 so that a user can distally advance or proximally retract the sleeve by manipulating a proximal end of the sleeve. In other embodiments, the sleeve extends over only a portion of the tube 120 or over only the tip 130 and the delivery device 100 includes an actuating mechanism that allows the sleeve to be advanced and retracted. The sleeve can be disposed over the tip 130 during insertion of the tip 130 to the target area to advantageously protect skin, tissue, and/or muscle along the insertion path from damage or injury from the rasping surface 134 and to allow the tip 130 to pass through the skin, tissue, and/or muscle more easily. Once the tip is positioned in the target location, the sleeve can be proximally retracted to expose the rasping surface 134 for decortication of the target area. After decortication and/or after delivery of the bone graft material, the sleeve can be distally advanced to cover the rasping surface 134 for withdrawal of the tip 130 from the body.

Figure 7A:
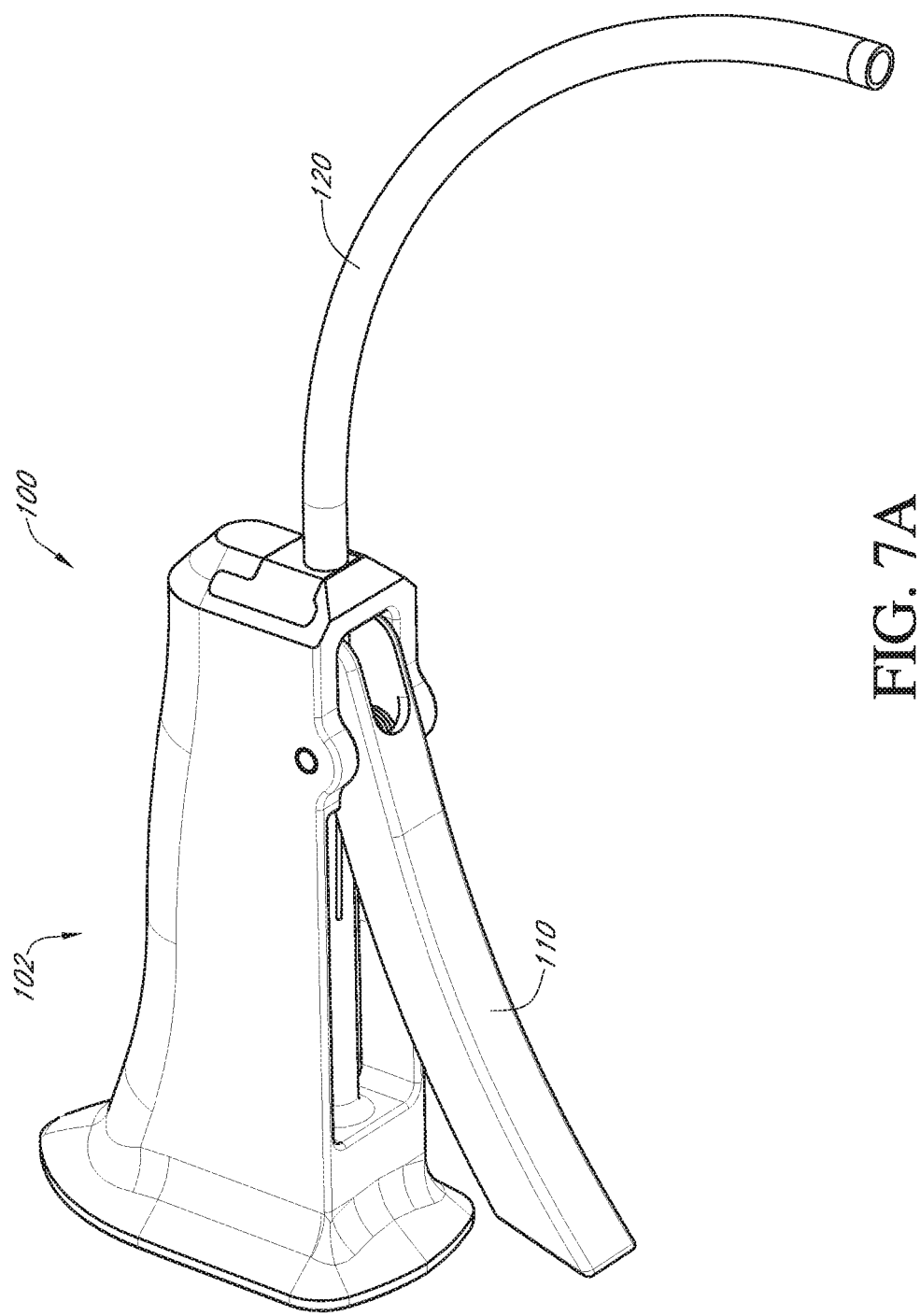
FIG. 7A illustrates a perspective view of an example embodiment of a bone graft delivery device.
Figure 7B:
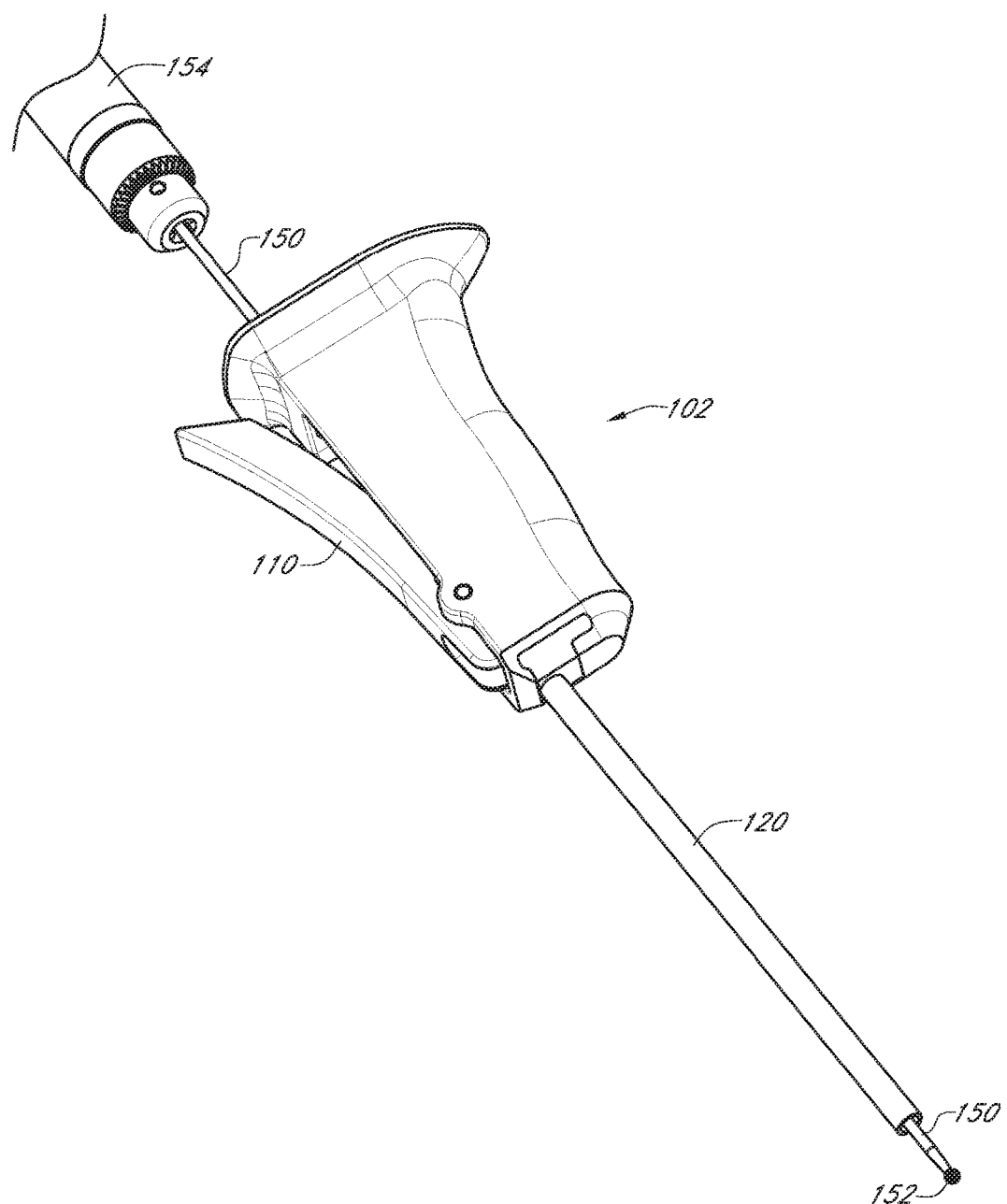
FIG. 7B illustrate the bone graft delivery device of FIG. 7A including a shaft having a distal burr disposed therethrough.
Figure 7C:
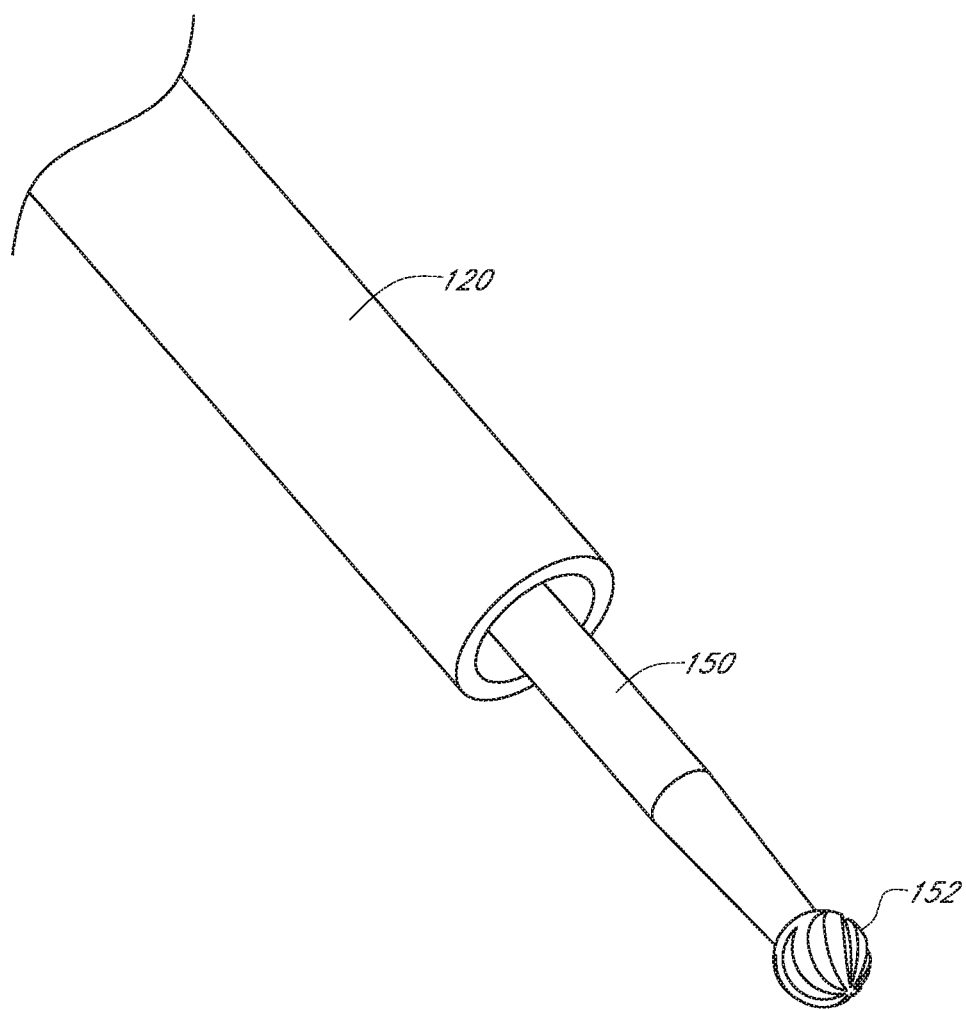
FIG. 7C illustrates an enlarged view of the distal end of the bone graft delivery device of FIG. 7B.

In some embodiments, the distal end of the tube 120 does not include a rasping tip 130 as shown in FIG. 7A. Instead, an elongate shaft 150 having a burr 152 at a distal end can be inserted through the tube 120 as needed or desired to decorticate a target area, for example as shown in FIGS. 7B and 7C. The use of a separate instrument for decortication can advantageously allow the user to select different burrs, rasps, or the like for different patients, target areas, or situations. The elongate shaft 150 and burr 152 can be operated manually. Alternatively, a proximal end of the shaft 150 can be coupled to a drill 154 or another device to provide decortication by mechanical, battery powered, electric, pneumatic, or any other means of force.

Figure 8:
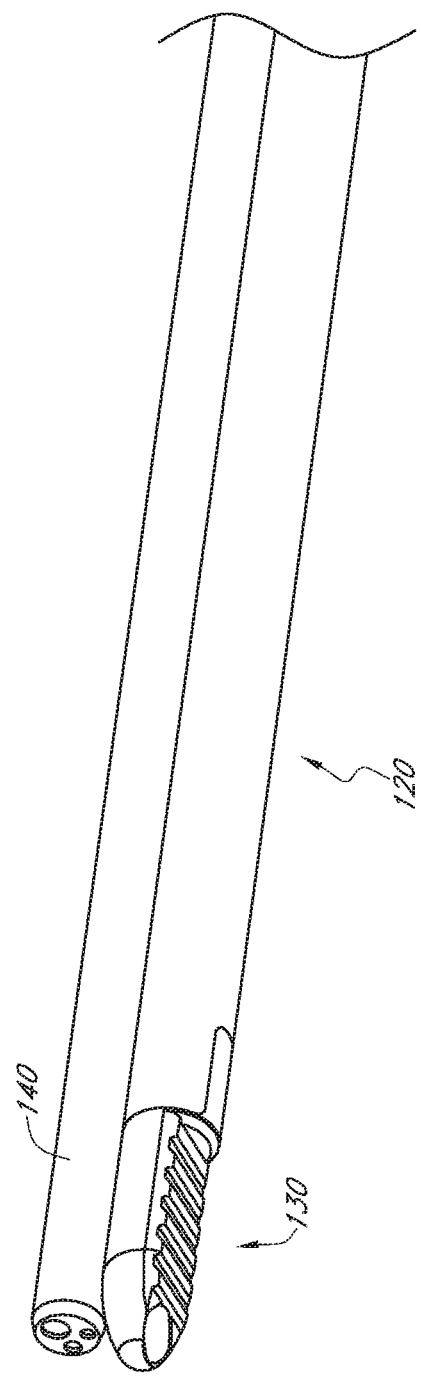
FIG. 8 illustrates a distal tip of an example embodiment of a bone graft delivery device including an endoscope.

The tip 130 may be made of a metallic, radiopaque material to facilitate visualization on, for example, fluoroscopy or x-ray. Alternatively, the tip 130 may be made of another material, for example a durable medical plastic or a composite material, and may include markers to facilitate visualization. In some embodiments, the bone graft delivery device 100 can include an endoscope or endoscopic camera to allow for visualization during insertion of the tip 130 to the target area, decortication, and/or delivery of the graft material. As shown in FIG. 8, an endoscope 140 can extend along the tube 120 and can be removably or permanently coupled to the tube 120.

In one embodiment, the device 100 described herein may be used in minimally invasive spinal surgery. For example, in a conventional posterolateral spine procedure, screws and or fusion cages may be delivered to adjacent vertebrae using small incisions made in a patient's back. It may additionally be desirable to deliver bone graft material to the surgical location, e.g., to the transverse processes, disc spaces, or facet joints, through one of these small incisions. The device described herein is sized to be delivered through a minimally invasive opening made in the patient's skin (e.g., through a skin incision of 4 cm or less), and configured so that the tip can be positioned adjacent a pedicle screw or other desired location. The curvature of the tube 120 can facilitate positioning of the tip 130 at desired spinal locations and allows, for example, insertion of the device 100 through an incision over one vertebra, and positioning of the tip 130 at an adjacent vertebra. Alternatively, the device can be delivered through any desired opening made in the patient's skin (e.g., minimally invasive or open). The jagged edges or other surface 134 on the device can be used to decorticate desired bone locations, causing bleeding of the bone and creating a surface that promotes bone fusion. The trigger 110 or other actuation mechanism can then be actuated to deliver bone graft material through the tube 120 lumen and openings 132 in the tip 130 to promote fusion of the bone.

Although use of the device 100 has been described with respect to an example spinal procedure, the device 100 can also be used in other spinal procedures and other orthopedic applications to deliver bone graft material to other locations in the body (for example, the femur or tibia).

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the invention are encompassed in the claim set listed below.

What is claimed is:

1. A method for delivering bone graft material to a surgical location, comprising:
   providing a bone graft delivery device comprising an elongate tube;
   removably coupling a distal tip to the bone graft delivery device, the distal tip having at least one opening for delivering the bone graft material to the surgical location;
   positioning the device adjacent the surgical location;
   decorticating bone with the distal tip; and
   delivering bone graft material through the tube and out the at least one opening of the tip.

2. The method of claim 1, wherein the bone graft material comprises autogenous, cadaveric and/or synthetic material.

3. The method of claim 1, wherein the bone graft delivery device is positioned at the surgical location through a minimally invasive opening in a patient's skin.

4. The method of claim 1, wherein the bone graft delivery device is positioned adjacent the spine and the distal tip decorticates a portion of the spine.

5. The method of claim 1, wherein decorticating bone with the distal tip comprises rasping bone with jagged edges of the distal tip.

6. The method of claim 1, wherein decorticating bone with the distal tip comprises actuating the distal tip by mechanical, battery powered, electric, pneumatic, or another means of force.

7. The method of claim 1, wherein the distal tip is generally bullet shaped.

8. The method of claim 1, wherein the distal tip is generally flat.

9. The method of claim 1, wherein the distal tip comprises at least one rasping surface configured to decorticate bone.

10. The method of claim 9, wherein the surface configured to decorticate bone extends proximally of the at least one opening.

11. The method of claim 1, wherein the distal tip is removably coupled to the distal end of the elongate tube.

12. The method of claim 1, wherein the distal tip is made of a radiopaque material.

13. The method of claim 1, wherein the distal tip comprises one or more radiopaque markers.

14. The method of claim 1, wherein the distal tip comprises a blunt end.

15. The method of claim 1, wherein the distal tip is positioned at a distal end of the elongate tube when the distal tip is removably coupled to the bone graft delivery device.

16. The method of claim 1, wherein the distal tip comprises a single monolithically formed piece.

17. The method of claim 1, wherein the distal tip is made of metal.

18. The method of claim 1, wherein the distal tip is made of a durable medical plastic.

19. The method of claim 1, wherein the distal tip is made of a composite material.

20. The method of claim 1, wherein the elongate tube is curved.

* * * * *